United States Patent [19]

Wasley et al.

[11] Patent Number: 5,096,919

[45] Date of Patent: Mar. 17, 1992

[54] PYRROLYLPHENYL-SUBSTITUTED HYDROXAMIC ACID DERIVATIVES

[75] Inventors: Jan W. F. Wasley, Chatham; Karl O. Gelotte, Watchung; Harold Meckler, Union, all of N.J.

[73] Assignee: Ciba-Geigy Corporation, Ardsley, N.Y.

[21] Appl. No.: 439,731

[22] Filed: Nov. 20, 1989

Related U.S. Application Data

[63] Continuation-in-part of Ser. No. 293,908, Jan. 5, 1989, abandoned.

[51] Int. Cl.$^5$ .................... A61K 31/40; C07D 207/30
[52] U.S. Cl. ..................................... 514/427; 548/561
[58] Field of Search .......................... 548/561; 514/427

[56] References Cited

U.S. PATENT DOCUMENTS

| 2,986,564 | 5/1961 | Rips | 548/561 |
| 3,868,391 | 2/1975 | Carney et al. | 548/561 |
| 4,782,085 | 11/1988 | Varma et al. | 514/507 |
| 4,792,560 | 12/1988 | Huang | 514/311 |

FOREIGN PATENT DOCUMENTS

| 196184 | 3/1986 | European Pat. Off. | 514/427 |
| 199151 | 4/1986 | European Pat. Off. | 514/427 |
| 248594 | 12/1987 | European Pat. Off. | 514/427 |
| 273451 | 2/1988 | European Pat. Off. | 514/427 |
| 279263 | 2/1988 | European Pat. Off. | 514/427 |
| 279281 | 2/1988 | European Pat. Off. | 514/427 |
| 292699 | 4/1988 | European Pat. Off. | 514/427 |
| 320628 | 11/1988 | European Pat. Off. | 514/427 |

OTHER PUBLICATIONS

J. Chem. Soc. Perkin Trans. I (1984) 2801.
J. Med. Chem., vol. 31, pp. 802–806 (1987).
J. Med. Chem., vol. 30, pp. 574–580 (1987).
J. Med. Chem., vol. 31, No. 3, pp. 499–500 (1988).
Biochemical Pharmacology, vol. 37, pp. 4531–4537 (1988).
Faseb J., vol. 2, A369 (Abstracts 427 and 428) (1988).
J. Med. Chem., vol. 31, pp. 1960–1964 (1988).

Primary Examiner—Mary C. Lee
Assistant Examiner—Robert C. Whittenbaugh
Attorney, Agent, or Firm—Norbert Gruenfeld

[57] ABSTRACT

Disclosed are the pyrrolylphenyl-substituted hydroxamic acid derivatives of the formula

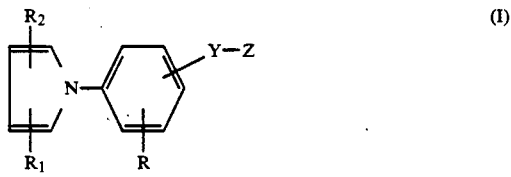

wherein R represents hydrogen, lower alkyl, halogen or lower alkoxy; $R_1$ and $R_2$ independently represent hydrogen, lower alkyl or aryl; Y represents a direct bond, lower alkylene, lower alkenylene, lower alkadienylene, (thio, sulfinyl or sulfonyl)-lower alkylene or oxy-lower alkylene; Z represents

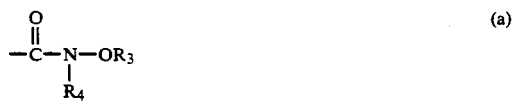

wherein $R_3$ represents hydrogen or acyl; $R_4$ represents lower alkyl, $C_3$-$C_7$-cycloalkyl, aryl or aryl-lower alkyl; or Z represents

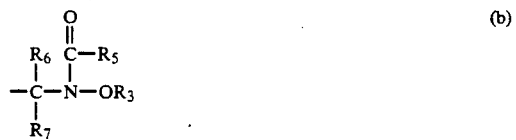

wherein $R_3$ represents hydrogen or acyl; $R_5$ represents lower alkyl, $C_3$-$C_7$-cycloalkyl, aryl, aryl-lower alkyl, amino or N-(mono- or di-lower alkyl)-amino; $R_6$ and $R_7$ represent hydrogen or lower alkyl; and pharmaceutically acceptable salts thereof provided that $R_3$ represents hydrogen; which are useful as selective lipoxygenase inhibitors, methods for preparation thereof, pharmaceutical compositions comprising said compounds, and a method of inhibiting lipoxygenase and of treating diseases in mammals which are responsive to lipoxygenase inhibition using said compounds and pharmaceutical compositions comprising said compounds of the invention.

22 Claims, No Drawings

PYRROLYLPHENYL-SUBSTITUTED HYDROXAMIC ACID DERIVATIVES

CROSS REFERENCE TO RELATED APPLICATIONS

This is a continuation-in-part of application Ser. No. 293,908 filed Jan. 5, 1989 now abandoned.

SUMMARY OF THE INVENTION

The invention relates to the pyrrolylphenyl-substituted hydroxamic acid derivatives as defined herein which are particularly useful as selective lipoxygenase inhibitors, methods for preparation thereof, pharmaceutical compositions comprising said compounds, and a method of inhibiting lipoxygenase and of treating diseases in mammals which are responsive to lipoxygenase inhibition using said compounds or pharmaceutical compositions comprising said compounds of the invention.

The compounds of the invention are particularly useful for the treatment of various inflammatory and allergic conditions, e.g. bronchial allergies and inflammatory disorders such as asthma, ocular allergies and inflammation, and dermatological allergies and inflammation such as psoriasis; also for the treatment of rheumatic disorders such as rheumatoid arthritis; and also for the treatment of ischemic conditions such as myocardial infarction and cerebral ischemia.

DETAILED DESCRIPTION OF THE INVENTION

More particularly the invention relates to the compounds of formula I

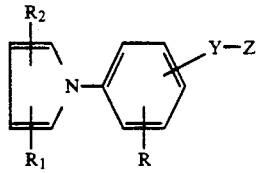

wherein R represents hydrogen, lower alkyl, halogen or lower alkoxy; $R_1$ and $R_2$ independently represent hydrogen, lower alkyl or aryl; Y represents a direct bond, lower alkylene, lower alkenylene, lower alkadienylene, (thio, sulfinyl or sulfonyl)-lower alkylene or oxy-lower alkylene; Z represents

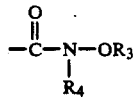

wherein $R_3$ represents hydrogen or acyl; $R_4$ represents lower alkyl, $C_3$–$C_7$-cycloalkyl, aryl or aryl-lower alkyl; or Z represents

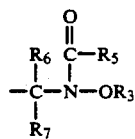

wherein $R_3$ represents hydrogen or acyl; $R_5$ represents lower alkyl, $C_3$–$C_7$-cycloalkyl, aryl, aryl-lower alkyl, amino or N-(mono- or di-lower alkyl)-amino; $R_6$ and $R_7$ represent hydrogen or lower alkyl; and pharmaceutically acceptable salts thereof provided that $R_3$ represents hydrogen.

A particular embodiment of the invention relates to the compounds of formula I wherein Z represents (a), i.e. of formula II

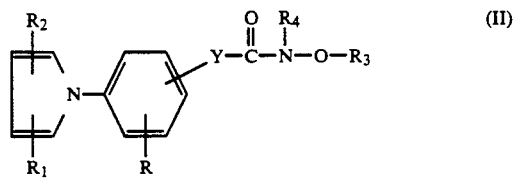

wherein R represents hydrogen, lower alkyl, halogen or lower alkoxy; $R_1$ and $R_2$ independently represent hydrogen, lower alkyl or aryl; $R_3$ represents hydrogen or acyl; $R_4$ represents lower alkyl, $C_3$–$C_7$-cycloalkyl, aryl or aryl-lower alkyl; Y represents a direct bond, lower alkylene, lower alkenylene, lower alkadienylene, (thio, sulfinyl or sulfonyl)-lower alkylene or oxy-lower alkylene; and pharmaceutically acceptable salts of said compounds provided that $R_3$ represents hydrogen.

Preferred are the compounds of formula II wherein Y represents lower alkenylene, lower alkadienylene, lower alkylene, thio-lower alkylene or oxy-lower alkylene; R represents hydrogen or halogen; $R_1$ and $R_2$ independently represent hydrogen or lower alkyl; $R_3$ represents hydrogen or acyl; $R_4$ represents lower alkyl; and pharmaceutically acceptable salts of said compounds provided that $R_3$ represents hydrogen.

Further preferred are said compounds of the formula II wherein Y represents lower alkenylene, lower alkylene or oxy-lower alkylene; R represents hydrogen; $R_1$ and $R_2$ represent hydrogen or lower alkyl; $R_3$ represents hydrogen, lower alkanoyl or aroyl; $R_4$ represents lower alkyl; and pharmaceutically acceptable salts thereof provided that $R_3$ represents hydrogen.

Particularly preferred are said compounds of formula II wherein Y represents lower alkenylene; and pharmaceutically acceptable salts thereof provided that $R_3$ represents hydrogen.

Also particularly preferred are said compounds of formula II wherein Y represents lower alkylene; and pharmaceutically acceptable salts thereof provided that $R_3$ represents hydrogen.

A particular preferred embodiment of the invention represented by compounds of formula II relates to the compounds of formula III

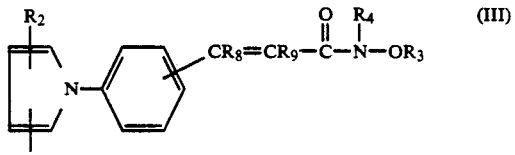

wherein $R_1$, $R_2$ and $R_8$ and $R_9$ independently represent hydrogen, methyl or ethyl; $R_4$ represents $C_1$–$C_3$-alkyl; $R_3$ represents hydrogen; and pharmaceutically acceptable salts thereof.

A further embodiment thereof relates to the compounds of formula IV

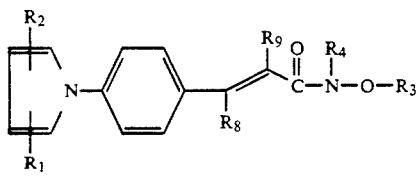

(IV)

wherein $R_1$–$R_4$, $R_8$ and $R_9$ have meaning as defined above for compounds of formula III; and pharmaceutically acceptable salts thereof.

Particularly preferred are said compounds wherein $R_1$, $R_2$ and $R_4$ represent methyl or ethyl; $R_3$, $R_8$ and $R_9$ represent hydrogen; and pharmaceutically acceptable salts thereof.

The invention also relates to the compounds of formula I wherein Z represents (b), i.e. of formula V

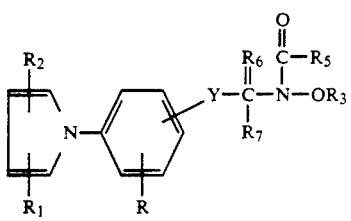

(V)

wherein R represents hydrogen, lower alkyl, halogen or lower alkoxy; $R_1$ and $R_2$ independently represent hydrogen, lower alkyl or aryl; Y represents a direct bond, lower alkylene, lower alkenylene, lower alkadienylene, (thio, sulfinyl or sulfonyl)-lower alkylene or oxy-lower alkylene; $R_3$ represents hydrogen or acyl; $R_5$ represents lower alkyl, $C_3$–$C_7$-cycloalkyl, aryl, aryl-lower alkyl, amino or N-(mono or di-lower alkyl)-amino; $R_6$ and $R_7$ represent hydrogen or lower alkyl; and pharmaceutically acceptable salts thereof provided that $R_3$ represents hydrogen.

Preferred are said compounds of formula V wherein Y represents a direct bond, thio-lower alkylene, oxy-lower alkylene, lower alkenylene or lower alkylene; R represents hydrogen; $R_1$ and $R_2$ independently represent hydrogen or lower alkyl; $R_3$ represents hydrogen, lower alkanoyl or aroyl; $R_5$ represents lower alkyl, aryl-lower alkyl, N-(mono- or di-lower alkyl)-amino or amino; $R_6$ represents hydrogen; $R_7$ represents hydrogen or lower alkyl; and pharmaceutically acceptable salts thereof provided that $R_3$ represents hydrogen.

Further preferred are said compounds wherein Y represents a direct bond, lower alkylene or lower alkenylene.

Particularly preferred are the compounds of the formula VI

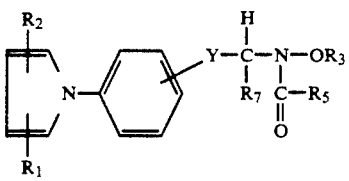

(VI)

wherein $R_1$ and $R_2$ represents hydrogen or lower alkyl; Y represents a direct bond, methylene or ethylene; $R_3$ represents hydrogen; $R_5$ represents $C_1$–$C_3$-alky,l, N-(mono- or di-lower alkyl)-amino or amino; $R_7$ represents hydrogen or $C_1$–$C_3$-alkyl; and pharmaceutically acceptable salts thereof.

Also preferred are the compounds of formula VII

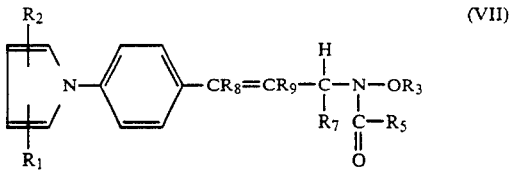

(VII)

wherein $R_1$, $R_2$, $R_7$, $R_8$ and $R_9$ represent hydrogen, methyl or ethyl; $R_3$ represents hydrogen; $R_5$ represents $C_1$–$C_3$-alkyl, N-(mono- or di-lower alkyl)-amino or amino; and pharmaceutically acceptable salts thereof.

Generally preferred are the compounds of the invention, e.g. of formula I, II, III, V and VI, wherein the point of attachment of the grouping Y is either meta or para to the pyrrole ring, and also said compounds wherein $R_1$ and $R_2$ are attached at the 2 and 5 positions of the pyrrole ring.

The general definitions used herein have the following meaning within the scope of the present invention.

The term "lower" referred to above and hereinafter in connection with organic radicals or compounds respectively defines such as branched or unbranched with up to and including 7, preferably up to and including 4 and advantageously one or two carbon atoms.

A lower alkyl group preferably contains 1–4 carbon atoms, advantageously 1–3 carbon atoms, and represents for example ethyl, propyl, butyl or most advantageously methyl.

A lower alkoxy group preferably contains 1–4 carbon atoms and represents for example ethoxy, propoxy, isopropoxy or advantageously methoxy.

Halogen preferably represents chloro or fluoro but may also be bromo or iodo.

Aryl represents preferably carbocyclic aryl.

Carbocyclic aryl represents for example phenyl or phenyl mono- or di-substituted by one or two radicals selected from lower alkyl, lower alkoxy, halogen, cyano and trifluoromethyl; or 1- or 2-naphthyl.

Aryl-lower alkyl represents for example benzyl or phenylethyl.

Acyl is preferably lower alkanoyl or aroyl.

Lower alkanoyl represents preferably $C_2$–$C_4$-alkanoyl such as acetyl or propionyl.

Aroyl represents preferably benzoyl or benzoyl mono- or di-substituted by one or two radicals selected from lower alkyl, lower alkoxy, halogen, cyano and trifluoromethyl; or 1- or 2-naphthoyl.

$C_3$–$C_7$-cycloalkyl represents cyclopropyl, cyclobutyl, cyclopentyl, cyclohexyl or cycloheptyl, preferably cyclohexyl or cyclopentyl.

Lower alkylene represents either straight chain or branched $C_1$–$C_7$-alkylene and represents preferably a methylene, ethylene, propylene or butylene chain, or said methylene, ethylene, propylene or butylene chain mono-substituted by $C_1$–$C_3$-alkyl or disubstituted on the same or different carbon atoms by $C_1$–$C_3$ alkyl (advantageously methyl), the total number of carbon atoms being up to and including 7.

Lower alkenylene represents $C_2$–$C_7$-alkenylene, may be straight chain or branched and represents preferably straight chain $C_2$–$C_4$-alkenylene or said straight chain $C_1$–$C_4$-alkenylene substituted on either saturated or unsaturated carbon atoms in the chain by one or two of $C_1$–$C_3$-alkyl, advantageously methyl, the total number of carbon atoms being up to and including 7.

Lower alkadienylene represents $C_4$–$C_7$-alkadienylene and represents preferably 1,3-butadienylene ($C_4$-alkadienylene), unsubstituted or substituted by $C_1$–$C_3$-alkyl (advantageously methyl), the total number of carbon atoms being up to and including 7.

Pharmaceutically acceptable salts of the acidic compounds of the invention (provided that $R_3$ represents hydrogen) are salts formed with bases, namely cationic salts such as alkali and alkaline earth metal salts, such as sodium, lithium, potassium, calcium, magnesium, as well as ammonium salts, such as ammonium, trimethylammonium, diethylammonium, tris-(hydroxymethyl)-methylammonium salts.

The compounds of the invention exhibit valuable pharmacological properties in mammals, and are particularly useful as selective 5-lipoxygenase inhibitors for the treatment of e.g. inflammatory, allergic and ischemic conditions.

The above-cited properties are demonstrable in in vitro and in vivo tests, using advantageously mammals, e.g. rats, guinea pigs, dogs, rabbits or isolated organs, tissues, and enzyme preparations thereof, as well as cells and fluids isolated from mammalian, including human, blood. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-8}$ molar concentrations. The dosage in vivo may range, depending on the route of administration, between about 0.01 and 30 mg/kg.

5-HETE and various leukotriene products are formed from arachidonic acid by means of the enzyme 5-lipoxygenase. Leukotrienes (LTs) $B_4$, $C_4$, $D_4$ and $E_4$ are a group of mediators with potent leukocyte-chemoattractant, smooth muscle-constricting and vascular permeability-enhancing properties. $LTB_4$ is among the most potent leukocyte chemotactic agents known. $LTC_4$, $LTD_4$ and $LTE_4$ are the components of the "slow-reacting substance of anaphylaxis" (SRS-A) and are potent inducers of broncho constriction that are released during an antigen challenge in lungs. Leukotrienes have been implicated in the pathogenesis of a variety of vascular and pulmonary disorders involving leukocyte and smooth muscle activation. Since these products are derived from the biotransformation of arachidonic acid (AA) through the 5-lipoxygenase pathway, selective inhibition of 5-lipoxygenase will suppress biosynthesis of leukotrienes in leukocytes and various organ systems.

5-Lipoxygenase inhibition is determined e.g. by measuring the percent inhibition of the synthesis of 5-HETE [(5S)-5-hydroxy-6,8,11,14-eicosa-tetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, essentially according to radiometric thin-layer chromatographic assays described by Walker and Dawson (J. Pharm. Pharmacol. 31: 778, 1979) and Jakschik and Lee (Nature 287: 51, 1980) used to measure the formation of 5-HETE and $LTB_4$-like products from $^{14}C$-arachidonic acid. $IC_{50}$ values are determined graphically as the concentration of test compound at which the synthesis of 5-HETE and $LTB_4$-like products is reduced to 50% of their respective control values.

The inhibition of $LTB_4$ formation can also be determined in vitro in whole blood from dogs. One ml samples of blood are preincubated at 37° C. for 5 minutes with the desired concentration of test compound added as a solution in 10 microliters of dimethylsulfoxide. $LTB_4$ synthesis is then stimulated by the addition of A-23187 and N-formyl-met-leu-phe (f-MLP). The amount of $LTB_4$ is measured in the separated plasma fraction by radioimmunoassay. $IC_{50}$ values are determined graphically as the concentration of test compound causing 50% inhibition of $LTB_4$ formation seen in control whole blood.

Furthermore, the inhibition of 5-lipoxygenase is determined after oral or i.v. administration to rats or dogs by measuring ex vivo in whole blood the decrease of A-23187-stimulated $LTB_4$ formation as compared to non-treated control animals.

Antiinflammatory activity is demonstrated by measuring the inhibition of the edema and inhibition of the influx of polymorphonuclear (PMN's) and mononuclear leucocytes (monocytes) after oral administration in the rat model in which pleurisy is first induced by injecting carrageenin into the pleural cavity, e.g. according to A. P. Almeida et al, J. Pharmacol. Exp. Therap. 214, 74 (1980).

Illustrative of the invention, the compound of example 1, (E)-3-[4-(2,5-dimethyl-1H-pyrrol-1-yl)-phenyl]-N-hydroxy-N-methyl-2-propenamide, inhibits the formation of 5-HETE [(5S)-5-hydroxy-6,8,11,14-eicosatetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, e.g. at an $IC_{50}$ of about 0.7 micromolar ($7 \times 10^{-7}$ M). Said compound also inhibits by 50% $LTB_4$ formation as determined ex vivo when administered at a dose of about 1 mg/kg p.o. to the dog.

Furthermore, the compound of example 1, at 10 mg/kg p.o. administered for two days at $-1$, 6, 24 and 45 hours relative to the carrageenin injection, causes inhibition of exudate volume and lowers the cell count of leukocytes 48 hours after injection of carrgeenin in the rat pleurisy model of inflammation.

The compounds of the invention are thus useful, particularly for the treatment and amelioration of diseases and conditions in mammals, including man, in which lipoxygenase activity or the accumulation of leukocytes (e.g. neutrophils) is involved, particularly allergic and inflammatory disorders, e.g. pulmonary allergies and inflammatory disorders (such as asthma), dermatological allergies and inflammatory disorders (such as psoriasis), also arthritic inflammatory disorders (such as rheumatoid arthritis), ocular allergies and inflammatory disorders, as well as ischemic conditions (such as in myocardial infarction).

The compounds of the invention, depending on the structural type involved, can be prepared by the following synthetic processes:

(1) for compounds of formula II (a) condensing a compound of formula VIII

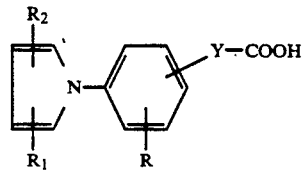

(VIII)

or a reactive functional derivative thereof, wherein R, $R_1$, $R_2$ and Y have meaning as defined hereinabove, with a compound of the formula IX $$R_4-NH-OR_3 \quad (IX)$$

wherein $R_3$ and $R_4$ have meaning as defined herein, optionally in protected form when $R_3$ represents hydrogen; and (2) for compounds of formula V (b) condensing a compound of the formula X

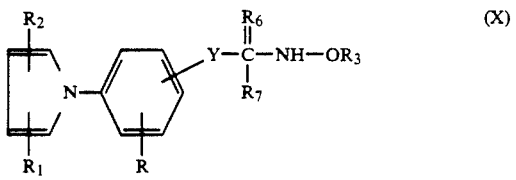

wherein R, $R_1$, $R_2$, $R_3$, $R_6$ and $R_7$ have meaning as defined hereinabove with a compound of the formula XI $$R_5-COOH \quad (XI)$$

or a reactive functional derivative thereof, wherein $R_5$ represents lower alkyl, $C_3$-$C_7$-cycloalkyl, aryl, aryl-lower alkyl or di-lower alkylamino; or (c) condensing a compound of the formula X above with phosgene followed by ammonia, a mono lower alkylamine or a di-lower alkylamine; or (d) condensing a compound of the formula X above with a lower alkyl isocyanate, or a tri(lower alkyl)-silyl isocyanate and subsequent removal of silyl protecting group; or (3) for compounds of formula I wherein Z has meaning of group (a) or (b) as defined above, (e) condensing a compound of the formula

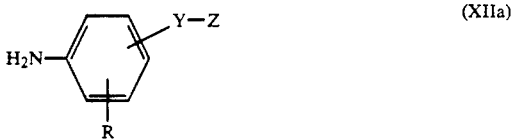

wherein Y, Z and R have meaning as defined above, and preferably wherein hydroxy groups are in protected form with a compound of the formula $$R_1-COCH_2CH_2CO-R_2 \quad (XIII)$$

or a compound of the formula

wherein $R_1$ and $R_2$ have meaning as previously defined, and $R_a$ and $R_b$ represent lower alkyl, and wherein in formula XIII or XIIIa, $R_1$ and $R_2$ may be located at other positions therein.

In the above cited processes, the said process is carried out while, if necessary, temporarily protecting any interfering reactive group(s), and then liberating the resulting compound of the invention; and, if required or desired, a resulting compound of the invention is converted into another compound of the invention, and/or, if desired, a resulting free compound is converted into a salt or a resulting salt is converted into a free compound or into another salt; and/or a mixture of isomers or racemates obtained is separated into the single isomers or racemates; and/or, if desired, a racemate is resolved into the optical antipodes.

In starting compounds and intermediates which are converted to the compounds of the invention in a manner described herein, functional groups present, such as amino and hydroxy groups, are optionally protected by conventional protecting groups that are common in preparative organic chemistry. Protected amino and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1984.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for examples the methyl or ethyl esters.

Also, a reactive esterified derivative of an alcohol in any of the processes cited herein represents said alcohol esterified by a strong acid, especially a strong inorganic acid, such as a hydrohalic acid, especially hydrochloric, hydroboromic or hydriodic acid, or sulphuric acid, or by a strong organic acid, especially a strong organic sulfonic acid, such as an aliphatic or aromatic sulfonic acid, for example methanesulfonic aid, 4-methylphenylsulfonic acid or 4-bromophenylsulfonic acid. A said reactive esterified derivative is especially halo, for example chloro, bromo or iodo, or aliphatically or aromatically substituted sulfonyloxy, for example methylsulfonyloxy or 4-methylphenylsulfonyloxy (tosyloxy).

The above processes for the synthesis of compounds of the invention can be carried out according to methodology generally known in the art for the preparation of hydroxamic acids and derivatives thereof.

The synthesis according to process (a) involving the condensation of a free carboxylic acid of formula VIII with an optionally hydroxy protected hydroxylamine derivative of formula IX can be carried out in the presence of a condensing agent, e.g. diethyl phosphorocyanidate, 1,1'-carbonyldi-imidazole or dicyclohexylcarbodiimide, in an inert polar solvent, such as dimethylformamide or methylene chloride.

The synthesis according to process (a) involving the condensation of a reactive functional derivative of an acid of formula VIII as defined above, e.g. an acid chloride or mixed anhydride with an optionally hydroxy protected hydroxylamine derivative of formula IX, or a salt thereof in presence of a base such as triethylamine can be carried out, at a temperature ranging preferably from about −78° to +75°, in an inert organic solvent such as dichloromethane or toluene.

The synthesis according to process (b) involving the condensation of a carboxylic acid of formula XI or a reactive functional derivative thereof with a hydroxylamine derivative of formula X (optionally hydroxy protected when $R_3$ represents hydrogen) is essentially carried out as generally described for process (a).

In the case of acylation of the compounds of formula X wherein $R_3$ represents hydrogen, e.g. with 2 mole equivalents or excess of a functional derivative of a compound of formula XI, the N,O-bis-acylated compounds of formula V, namely those wherein $R_3$ represents $COR_5$, are obtained. The N,O-diacylated compounds of formula V, e.g. wherein $R_5$ represents lower alkyl and $R_3$ represents the corresponding $COR_5$ group, can be selectively O-deacylated under basic conditions, e.g. with potassium carbonate in a hydroxylic solvent such as methanol to yield the corresponding compounds of formula V wherein $R_3$ represents hydrogen.

Processes c) and d) are directed to the preparation of urea derivatives, the compounds of formula I wherein Z represents group (b), i.e. of formula V wherein $R_5$ represents amino or substituted amino, from hydroxylamines of formula X.

The preparation according to process c) can be carried out by reacting the hydroxylamine derivative of formula X, preferably in hydroxy-protected form, with phosgene in an inert solvent such as toluene in the presence of e.g. triethylamine, followed by condensation with the appropriate amine at a temperature of about −25° C. to +50° C.

The preparation according to process d) involves the condensation of a hydroxylamine of formula X, preferably in hydroxy-protected form, with a lower alkyl isocyanate in an inert solvent such as toluene at a temperature ranging from room temperature to reflux temperature.

The process according to process (e) is carried out in an inert solvent such as toluene, optionally in the presence of an anhydrous acid so as to form the pyrrolyl substituted compounds wherein $R_1$ and $R_2$ are located at the 2 and 5 positions of the pyrrole ring. Compounds wherein $R_1$ and $R_2$ represent lower alkyl at other positions can be prepared from compounds wherein, in formula XIII or XIIIa, $R_1$ and $R_2$ are located at appropriate positions.

Protected forms of hydroxylamines of formula IX and X (wherein $R_3$ represents hydrogen) in the above processes are those wherein the hydroxy group is protected for example as a benzyl ether or tetrahydropyranyl ether. Removal of said protecting groups is carried out according to methods well known in the art, e.g. hydrogenolysis or acid hydrolysis, respectively.

The starting materials of formula VIII can be prepared e.g. by condensing an ester of a compound of the formula

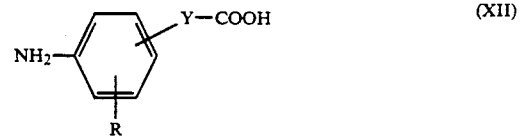

wherein R and Y have meaning as defined hereinabove with a compound of the formula

$$R_1—COCH_2CH_2CO—R_2 \qquad (XIII)$$

or a compound of the formula

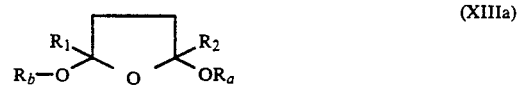

wherein $R_1$ and $R_2$ have meaning as previously defined, and $R_a$ and $R_b$ represent lower alkyl, in an inert solvent such as toluene, optionally in the presence of an anhydrous acid so as to form the pyrrolyl substituted compounds wherein $R_1$ and $R_2$ are located at the 2 and 5 positions of the pyrrole ring. Starting materials wherein $R_1$ and $R_2$ represent lower alkyl at other positions can be prepared from compounds wherein, in formula XIII or XIIIa, $R_1$ and $R_2$ are located at appropriate positions.

The acids of formula XII, diketones or dialdehydes of formula XIII and tetrahydrofuran derivatives of formula XIIIa are either known in the art or can be prepared according to methods known in the art.

The starting materials of formula VIII for the preparation of e.g. of compounds of formula III can also be prepared by condensing a compound of formula XIV

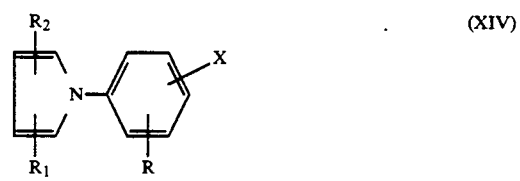

wherein $R_1$ and $R_2$ have meaning as defined hereinabove and X represents halogen, e.g. bromo, with an optionally substituted acrylic acid or a functional derivative thereof under conditions of the Heck reaction, e.g. in the presence of palladium chloride and tri-0-tolylphosphine.

The hydroxylamine derivatives of formula IX are known or are prepared according to methods well-known in the art for the preparation of hydroxylamines e.g. by condensing corresponding halides with e.g. benzyl or tetrahydropyranyl O-protected hydroxylamine, by reduction of oximes or reduction of nitro compounds (particularly if $R_4$ represents aryl).

The starting hydroxylamines of formula X may be prepared from a corresponding reactive derivative of an alcohol of formula XV

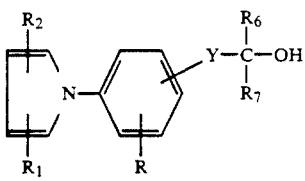

wherein R, $R_1$, $R_2$, Y, $R_6$ and $R_7$ have meaning as defined herein, such as the corresponding bromide, tosylate or mesylate derivative, by condensing such with e.g. O-benzylhydroxylamine or O-tetrahydropyranyl-hydroxylamine.

Alternately hydroxylamines of formula X wherein at least one of $R_6$ and $R_7$ represents hydrogen can be prepared from the corresponding aldehyde or ketone by conversion to the oxime with e.g. hydroxylamine hydrochloride according to known methods, followed by reduction to the hydroxylamine with e.g. diborane or sodium cyanoborohydride in acidic medium.

The alcohols of formula XV or corresponding aldehydes or ketones may be prepared e.g. from the corresponding acids of formula VIII or ester derivatives thereof according to methods well-known in the art. For example, such can be reduced to the alcohol wherein $R_6$ and $R_7$ represent hydrogen using an appropriate reducing agent such as lithium aluminum hydride, aluminum hydride and the like. Alternately the intermediates of formula XV may be prepared from the corresponding anilines by condensation thereof with a compound of formula XIII or XIIIa as described hereinabove for the preparation of intermediates of formula VIII.

The carboxylic acids of formula XI and reactive derivatives thereof are known in the art or can be prepared according to methods well-known in the art.

Starting materials of formula XIIa for process (e) can be prepared according to processes (a), (b), (c) or (d) starting with appropriate protected aniline derivatives in reaction sequences described above.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Advantageously those starting materials are used in said reactions that lead to the formation of those compounds indicated above as being preferred.

Compounds of the invention can also be converted into each other according to methods generally known per se, e.g. by hydrogenation of one or more double bonds.

Furthermore, compounds of formula I wherein $R_3$ represents hydrogen can be converted to compounds of formula I wherein $R_3$ represents acyl using conventional O-acylation methods. Conversely, compounds of formula I wherein $R_3$ represents acyl can be converted to compounds of formula I wherein $R_3$ represents hydrogen using conventional methods of ester hydrolysis.

The invention also relates to any novel starting materials and processes for their manufacture.

Depending on the choice of starting materials and methods, the new compounds may be in the form of one of the possible isomers or mixtures thereof, for example, as substantially pure geometric (Z or E, cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, in known manner, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diasteroisomeric salts thereof, obtained with an optically active acid or base, and liberating the optically active acidic or basic compound. The hydroxamic acids (wherein $R_3$ represents hydrogen) can thus be resolved into their optical antipodes e.g. by fractional crystallization of d- or l-(alpha-methylbenzylamine, cinchonidine, cinchonine, quinine, quinidine, ephedrine, dehydroabietylamine, brucine or strychnine)-salts.

Finally, acidic compounds of the invention are either obtained in the free form, or as a salt thereof.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit 5-lipoxygenase and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1% to 75%, preferably about 1% to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The invention also relates to a method of inhibiting 5-lipoxygenase activity in mammals and treating diseases and conditions responsive thereto, particularly inflammatory and allergic disorders, which comprises administering to a mammal in need thereof an effective amount of a compound of the invention or of a pharmaceutical composition comprising a said compound in combination with one or more pharmaceutically acceptable carriers.

The dosage of active compound administered is dependent on the species of warm-blooded animal (mammal), the body weight, age and individual condition, and on the form of administration.

A unit dosage for a mammal of about 50 to 70 kg may contain between about 10 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR).

EXAMPLE 1

(a) A solution of 12.05 g of (E)-3-[4-(2,5-dimethyl-1H-pyrrol-1-yl)-phenyl]-2-propenoic acid in 350 ml of dichloromethane and 9.7 ml triethylamine, is cooled in an ice bath. To this stirred solution is added 7.0 ml of ethyl chloroformate dropwise. After four hours at ice-bath temperature, 20.7 ml of triethylamine is added, followed by 12.6 g of N-methylhydroxylamine hydrochloride and the mixture is kept at room temperature for 16 hours. This mixture is washed with cold 0.3 N aqueous hydrochloric acid, ice cold sodium bicarbonate and brine. The organic phase is dried over MgSO$_4$, treated with charcoal and filtered. The solvent is evaporated at 50° under reduced pressure and the product is crystallized from ether to give (E)-3-[4-(2,5-dimethyl-1H-pyrrol-1-yl)-phenyl]-N-hydroxy-N-methyl-2-propenamide, m.p. 143°-145°, the compound of formula IV wherein $R_1$ and $R_2$ represent methyl at the 2 and 5 positions, $R_4$ represents methyl, and $R_3$, $R_8$ and $R_9$ represent hydrogen; the compound may also be named (E)-3-[4-(2,5-dimethyl-1H-pyrrol-1-yl)-phenyl]-N-methyl-2-propenohydroxamic acid. The product can also be recrystallized from ethyl acetate (with charcoal and silica gel).

(b) The sodium salt is prepared as follows:

A solution of 7.4 ml of 1N sodium hydroxide in methanol is added to a solution of 2.0 g. of the hydroxamic acid in 50 ml of dichloromethane. This solution is evaporated at 60° under reduced pressure to give sodium (E)-3-[4-(2,5-di-methyl-1H-pyrrol-1-yl)-phenyl]-N-methyl-2-propenohydroxamate, m.p. 235°.

(c) Similarly prepared is potassium (E)-3-[4-(2,5-dimethyl-1H-pyrrol-1-yl)-phenyl]-N-methyl-2-propeno-hydroxamate, m.p. 200°-202°.

(d) The tromethamine salt is prepared as follows:

(E)-3-[4-(2,5-dimethyl-1H-pyrrol-1-yl)phenyl]-N-methyl-2-propenohydroxamic acid (1.85 g) is added to a solution of 0.85 g of tromethamine in 150 ml of methanol. The resulting solution is treated with charcoal, filtered and evaporated to dryness. The residue is crystallized from ether to obtain (E)-3-[4-(2,5-dimethyl-1H-pyrrol-1-yl)phenyl]-N-methyl-2-propenohydroxamic acid tromethamine salt, m.p. 134°-136°.

The starting material is prepared as follows:

A mixture of 21.4 g of methyl 4-aminocinnamate and 50 g of acetonylacetone in 500 ml of toluene is heated under reflux using a Dean Stark water separator for 16 hours. The solution is washed with ice cold dilute hydrochloric acid, brine, and then dried over magnesium sulfate. The organic phase is filtered through silica gel, evaporated at 60° under reduced pressure and the residue is crystallized from hexane to yield methyl 4-(2,5-dimethyl-1H-pyrrol-1-yl)-cinnamate, m.p. 73°-75°. A solution of the ester in 150 ml of methanol and 100 ml 1N aqueous sodium hydroxide is stirred at room temperature for 16 hours. Methanol is evaporated at 60° under reduced pressure. The basic solution is washed with ethyl acetate, then made acidic with ice cold 5N aqueous hydroxloric acid, and extracted with ethyl acetate. The extract is washed with brine, dried over magnesium sulfate, treated with charcoal, and evaporated to dryness at 60° under reduced pressure. The residue is crystallized from ether/hexane (2:1) to yield (E)-4-(2,5-di-methyl-1H-pyrrol-1-yl)-cinnamic acid, m.p. 189°-191°, also named (E)-3-[4-(2,5-dimethyl-1H-pyrrol-1-yl)-phenyl]-2-propenoic acid.

3-[4-(2,5-Dimethyl-1H-pyrrol-1-yl)phenyl]-2-propenoic acid can also be prepared as follows:

To a stirred solution of 50.0 g 1-(4-bromophenyl)-2,5-dimethylpyrrole (Meakins et al, J. Chem. Soc., Perkin Trans. I, 1984, 2801-2807) and tri-O-tolylphosphine (2.5 g) in triethylamine (100.0 ml), under a nitrogen atmosphere, is added decolorizing carbon (5.0 g) and palladium chloride (0.35 g). To this stirred slurry is added acrylic acid (20.0 g) followed by triethylamine (39.0 ml). The reaction mixture is refluxed for 4.5 hours, cooled to room temperature and diluted with water (700 ml). The pH of the reaction mixture is adjusted to ca. 2 by the slow addition of concentrated hydrochloric acid (63 ml). The solids are collected by filtration and the filter cake is washed with water until the pH is ca. 7 and then dried. The dried filter cake is suspended in boiling ethanol (350 ml), clarified, cooled to room temperature and diluted with water (450 ml) to induce crystallization. The slurry is cooled to −10° C. and the product collected by filtration. The filter cake is dried in vacuo at 45°. The dried solid is slurried in cold toluene, filtered and to dried to afford 3-[4-(2,5-dimethyl-1H-pyrrol-1-yl)phenyl)-2-propenoic acid, m.p. 184°–185°.

EXAMPLE 2

A solution of 1.0 g of 2-[4-(2,5-dimethyl-1H-pyrrol-1-yl)-phenylthio]-acetic acid in 75 ml of dichloromethane and 0.8 ml. triethylamine, is cooled in an ice bath. To this solution is added 0.5 ml of trimethylacetyl chloride and the solution is stirred at room temperature overnight. Triethylamine (2 ml) is added followed by 1 g of N-methylhydroxylamine hydrochloride and the mixture is kept at room temperature for 20 hours. The mixture is washed with 0.3 N aqueous hydrochloric acid, ice cold dilute sodium bicarbonate and brine. The organic phase is dried over $MgSO_4$ and filtered. The solvent is evaporated at 50° at reduced pressure, the residue is dissolved in diethyl ether and the solutions filtered through 10 g of silica gel to yield 2-[4-(2,5-dimethyl-1H-pyrrol-1-yl)phenylthio]-N-hydroxy-N-methylacetamide; NMR (DMSO-$d_6$: $\delta$7.1, 5.85, 3.25, 1.95.

The starting material is prepared by treatment of ethyl 4-aminophenylthioacetate with acetonylacetone according to previously described procedure to yield ethyl 2-[4-(2,5-dimethyl-1H-pyrrol-1-yl)-phenylthio]-acetate which is then hydrolyzed to the acid.

EXAMPLE 3

Prepared in a similar manner as described in the previous examples are:

(a) 2-[4-(2,5-dimethyl-1-H-pyrrol-1-yl)-phenoxy]-N-hydroxy-N,2-dimethylpropanamide, m.p. 122°–124°.

The starting material is prepared as follows:

A mixture of 4.0 g of p-aminophenol and 4.0 g of acetonylacetone is heated under reflux in toluene for 3 hours using a Dean Stark water separator to yield 4-(2,5-dimethyl-1H-pyrrol-1-yl)-phenol. Condensation with ethyl alpha-bromoisobutyrate in ethyl alcohol in the presence of potassium carbonate gives ethyl 2-[4-(2,5-di-methyl-1H-pyrrol-1-yl)-phenoxy]-2-methylpropanoate. Hydrolysis with 1.5 N sodium hydroxide solution yields 2-[4-(2,5-dimethyl-1H-pyrrol-1-yl)-phenoxy]-2-methyl-propanoic acid, m.p. 178°–180°.

(b) 2-[4-(2,5-dimethyl-1H-pyrrol-1-yl)-phenoxy]-N-hydroxy-N-methylacetamide, m.p. 148°–150°.

The starting material is prepared as described under (a) using ethyl bromoacetate instead of ethyl alpha-bromo isobutyrate.

(c) 3-[4-(2,5-dimethyl-1H-pyrrol-1-yl)-phenyl]-N-hydroxy-N-methylpropanamide, oil; NMR (DMSO-$d_6$): $\delta$7.1, 7.3, 5.85, 3.25, 2.0.

The starting material is prepared as follows:

A solution of (E)-3-[4-(2,5-dimethyl-1H-pyrrol-1-yl)-phenyl]-2-propenoic acid in ethyl acetate is hydrogenated at 3 atmospheres pressure using 10% palladium on charcoal to yield 3-[4-(2,5-dimethyl-1H-pyrrol-1-yl)-phenyl]-propanoic acid, as an oil.

(d) 2-[4-(2,5-dimethyl-1H-pyrrol-1-yl)phenyl]-N-hydroxy-N-methylacetamide, oil; NMR (DMSO-$d_6$): $\delta$7.15, 7.35, 5.85, 3.4, 2.0.

The starting material is prepared from ethyl 4-aminophenylacetate and acetonylacetone according to previously described procedures for a similar condensation.

(e) 5-[4-(2,5-dimethyl-1H-pyrrol-1-yl)-phenyl]-N-hydroxy-N-methylvaleramide; oil, NMR (DMSO-$d_6$): $\delta$7.1, 7.25, 5.88, 3.3, 2.0.

The starting material is prepared as follows:

Triethyl 4-phosphonocrotonate is condensed with p-nitrobenzaldehyde in the presence of sodium hydride in toluene/tetrahydrofuran to yield 5-(p-nitrophenyl)-penta-2,4-dienoic acid ethyl ester, m.p. 150°–152°. Hydrogenation in ethyl acetate at one atmosphere pressure and room temperature using Adams catalyst yields ethyl 5-(4-amino-phenyl)-valerate. Condensation with acetonylacetone yields ethyl 5-[4-(2,5-dimethyl-1H-pyrrol-1-yl)-phenyl]-valerate.

(f) (E)-3-[4-(1H-pyrrol-1-yl)-phenyl]-N-hydroxy-N-methyl-2-propenamide.

The starting material is prepared by condensing methyl 4-aminocinnamate with 2,5-diethoxytetrahydrofuran in glacial acetic acid under reflux for 1 hour. See e.g. J. Med. Chem. 31, 802 (1988).

(g) 3-[4-(1H-pyrrol-1-yl)-phenyl]-N-hydroxy-N-methyl-propanamide by hydrogenation of the compound under (f).

(h) 2-[4-(1H-pyrrol-1-yl)-phenyl]-N-hydroxy-N-methyl acetamide.

The starting material is prepared by condensing ethyl p-aminophenylacetate with 2,5-diethoxytetrahydrofuran.

(i) 2-[4-(2,5-dimethyl-1H-pyrrol-1-yl)-3-chloro-phenyl-N-hydroxy-N-methylpropanamide.

The starting material is prepared from ethyl alpha-(3-chloro-4-aminophenyl)-propionate (U.S. Pat. No. 3,868,391) and acetonylacetone.

j) 2-[3-(1H-pyrrol-1-yl)-phenyl]-N-hydroxy-N-methyl acetamide. The starting material is prepared from methyl 3-(1H-pyrrol-1-yl)-phenylacetate (J. Med. Chem. 31, 802 (1988)) and acetonylacetone.

EXAMPLE 4 a) Acetyl chloride (1 ml) is added while stirring to a solution of 1.4 g of N-hydroxy-1-[4-(2,5-dimethyl-1H-pyr-rol-1-yl)-phenyl]-ethylamine and 2 ml of triethylamine in 100 ml of methylene chloride at 0°. The reaction mixture is stirred for 2 hours, washed with ice cold dilute hydrochloric acid, water, dried over magnesium sulfate, treated with charcoal, filtered and evaporated to dryness to yield N-acetyl-N-acetyloxy-1-[4-(2,5-dimethyl-1H-pyrrol-1-yl)-phenyl]-ethylamine as an oil.

The starting material is prepared as follows:

A mixture of 4.0 g of p-aminoacetophenone and 4.0 g of acetonylacetone is heated under reflux for 4 hours, and filtered to yield 4-(2,5-dimethyl-1H-pyrrol-1-yl)-acetophenone.

A mixture of 4-(2,5-dimethyl-1H-pyrrol-1-yl)-acetophenone (22.7 g), hydroxylamine hydrochloride (25.0 g), pyridine (130 ml) in 100 ml of methanol is heated under reflux for 20 hours. Workup in the usual manner yields 4-(2,5-dimethyl-1H-pyrrol-1-yl)-acetophenone oxime.

Sodium cyanoborohydride (6.9 g) is added to a mixture of 4-(2,5-dimethyl-1H-pyrrol-1-yl)-acetophenone oxime in 400 ml of methanol and ethanolic hydrochloric acid is added to adjust to pH 3. The reaction mixture is stirred at room temperature overnight, poured over ice, rendered basic and extracted with ether. The ether extract is washed with brine, dried and evaporated to dryness. The residue is chromatographed over silica gel first with methylene chloride and then with 15% methanol, 85% methylene chloride to yield in fractions obtained with second eluent N-hydroxy-1-[4-(2,5-dimethyl-1H-pyrrol-1-yl)-phenyl]-ethyl-amine, m.p. 109°–111°.

b) Similarly prepared is N-acetyl-N-acetyloxy-1-[3-(2,5-dimethyl-1H-pyrrol-1-yl)-phenyl]-ethylamine as an oil.

c) Similarly prepared is N-benzoyl-N-benzoyloxy-1-[4-(2,5-dimethyl-1H-pyrrol-1-yl)-phenyl]-ethylamine.

d) Similarly prepared is N-(N',N'-dimethylcarbamoyl)-N-(N,N'-dimethylcarbamoyloxy)-1-[4-(2,5-dimethyl-1H-pyrrol-1-yl)-phenyl]-ethylamine using dimethylcarbamyl chloride as the acylating agent.

e) Similarly prepared is N-acetyl-N-acetyloxy-[4-(2,5-dimethyl-1H-pyrrol-1-yl)-cinnamylamine. The starting material is prepared by first condensing p-amino-benzaldehyde with acetonylacetone to obtain 4-(2,5-dimethyl-1H-pyrrol-1-yl)-benzaldehyde which is in turn condensed with diethyl phosphonoacetaldehyde diethylacetal to obtain 4-(2,5-dimethyl-1H-pyrrol-1-yl)-cinnamaldehyde. The aldehyde is then converted to the oxime and reduced to the hydroxylamine according to previously described procedures.

EXAMPLE 5 a) A mixture of 1.4 g of N-acetyl-N-acetyloxy-1-[4-(2,5-dimethyl-1H-pyrrol-1-yl)-phenyl]-ethylamine and 7.0 g of potassium carbonate in 70 ml of methanol is stirred at room temperature overnight and then evaporated to dryness. The residue is suspended in water and the product is extracted with ethyl acetate. The ethylacetate extract is washed with brine, dried and evaporated to dryness. The residue is purified by chromatography on silica gel to yield N-acetyl-N-hydroxy-1-[4-(2,5-dimethyl-1H-pyrrol-1-yl)-phenyl]-ethylamine; NMR (DMSO-$d_6$): δ7.15, 7.45, 5.85, 2.0, 2.15.

b) Similarly prepared is N-acetyl-N-hydroxy-1-[3-(2,5-dimethyl-1H-pyrrol-1-yl)-phenyl]-ethylamine; NMR (DMSO-$d_6$): δ7.1–7.5, 5.85, 2.0, 2.15.

c) Similarly prepared is N-benzoyl-N-hydroxy-1-[4-(2,5-dimethyl-1H-pyrrol-1-yl)-phenyl]-ethylamine.

d) Similarly prepared is N-acetyl-N-hydroxy-[4-(2,5-dimethyl-1H-pyrrol-1-yl)-cinnamylamine.

EXAMPLE 6 a) A solution of 1.4 g of N-hydroxy-1-[4-(2,5-dimethyl-1H-pyrrol-1-yl)-phenyl]-ethylamine in 60 ml of toluene is stirred and treated first with one mole equivalent of 4.0 M ethanolic HCl, followed by 15 ml of 2.0 M phosgene in toluene. The solution is stirred for 7 hours, 50 ml of concentrated ammonium hydroxide is added and the mixture is stirred overnight. Excess water is then added and the mixture is again stirred for 2 hours. The organic layer is separated, washed with brine, dried over magnesium sulfate, treated with charcoal and evaporated to dryness. The residue is crystallized from ether to yield N-carbamoyl-N-hydroxy-1-[4-(2,5-dimethyl-1H-pyrrol-1-yl)-phenyl]-ethyl-amine;

b) Similarly prepared is N-carbamoyl-N-hydroxy-[4-(2,5-dimethyl-1H-pyrrol-1-yl)-cinnamylamine.

N-Carbamoyl-N-hydroxy-4-(2,5-dimethyl-1H-pyrrol-1-yl)-cinnamylamine can also be prepared as follows:

A mixture of 1.1 g of N-hydroxy-4-(2,5-dimethyl-1H-pyrrol-1-yl)-cinnamylamine and 5 ml of trimethylsilyl isocyanate in 100 ml ether is stirred at room temperature overnight. Water is added, the mixture is stirred for an additional 4 hours, the ether layer is separated, washed, dried and evaporated to dryness. The residue is purified by chromatography to yield the product as a thick oil; IR 1685, 1662, 970 $cm^{-1}$.

c) Similarly prepared is N-carbamoyl-N-hydroxy-4-(2,5-dimethyl-1H-pyrrol-1-yl)-alpha-methylcinnamylamine, m.p. 94°.

The starting material is prepared as follows:

A mixture of 4-(2,5-dimethyl-1H-pyrrol-1-yl)-benzaldehyde (2.8 g), 5.0 g of 1-triphenylphosphoranylidene-2-propanone and 120 ml of tetrahydrofuran is treated under reflux for 3 days. The mixture is evaporated to dryness, the residue is stirred in hexane and the suspension filtered. The hexane solution is evaporated to a small volume leading to crystallization of 1-[4-(2,5-dimethyl-1H-pyrrol-1-yl)]-buten-3-one, m.p. 108°–110°, which is in turn converted to the corresponding oxime and reduced to the hydroxylamine.

EXAMPLE 7 a) A solution of 0.7 g of N-(N'-methylcarbamoyl)-N-benzyloxy-1-[4-(2,5-dimethyl-1H-pyrrol-1-yl)-phenyl]-ethyl-amine in 50 ml of ethyl acetate is hydrogenated at room temperature and 3 atmospheres pressure for 3 hours to yield N-(N'-methylcarbamoyl)-N-hydroxy-1-[4-(2,5-dimethyl-1H-pyrrol-1-yl)-phenyl]-ethylamine; m.p. 131°–133°.

The starting material is prepared as follows:

O-Benzylhydroxylamine hydrochloride (7.7 g) is added to a solution of 9.0 g of 4-(2,5-dimethyl-1H-pyrrol-1-yl)-acetophenone in 200 ml of methanol, and the mixture is stirred for 3 hours. The solvent is removed under reduced pressure, the residue is dissolved in 300 ml of hexane and the solution is washed first with 2N aqueous hydrochloric acid and then brine. The organic layer is dried over magnesium sulfate, treated with charcoal and evaporated to dryness to yield O-benzyl 4-(2,5-dimethyl-1H-pyrrol-1-yl)-acetophenone oxime.

A solution of 6.6 g of O-benzyl 4-(2,5-dimethyl-1H-pyrrol-1-yl)-acetophenone oxime in 150 ml ethyl acetate is treated with 8 g of borane-pyridine complex followed by 45 ml of 6N aqueous hydrochloric acid. The mixture is stirred for 16 hours, poured over ice, made alkaline to pH 9 and extracted with ether. The ether extract is washed with brine, dried over magnesium sulfate and filtered to yield N-benzyloxy-1-[4-(2,5-dimethyl-1H-pyrrol-1-yl)-phenyl]-ethylamine.

Methyl isocyanate (5 ml) is added to a solution of 2.1 g of N-benzyloxy-1-[4-(2,5-dimethyl-1H-pyrrol-1-yl)-phenyl]-ethylamine in 200 ml of ether and the solution is stirred at room temperature for 24 hours. Excess water is added and the mixture is stirred for 3 hours. The organic layer is separated, washed with brine, dried over magnesium sulfate and evaporated to dryness. The residue is crystallized from ether-hexane (3:1) to yield N-(N'-methylcarbamoyl)-N-benzyl-oxy-1-[4-(2,5-dimethyl-1H-pyrrol-1-yl)-phenyl]-ethylamine, m.p. 140°–142°.

b) Similarly prepared is N-(N'-methylcarbamoyl)-N-hydroxy-4-(2,5-dimethyl-1H-pyrrol-1-yl)-cinnamylamine, m.p. 73°-75°.

EXAMPLE 8

Triethylamine (2.06 g) is added to a mixture of 5.0 g of (E)-3-[4-(2,5-dimethyl-1H-pyrrol-1-yl)-phenyl]-N-hydroxy-N-methyl-2-propenamide in 100 ml of methylene chloride and the mixture is stirred for 15 minutes. Acetic anhydride (2.07 g) is added and the mixture is stirred at room temperature overnight. The reaction mixture is washed with water and sodium bicarbonate solution, the organic layer is separated, treated with charcoal, dried and evaporated to dryness. The residue is crystallized from ethanol, water (1:1) to yield (E)-3-[4-(2,5-dimethyl-1H-pyrrol-1-yl)-phenyl]-N-acetoxy-N-methyl-2-propenamide, m.p. 120°-121°.

EXAMPLE 9

A mixture of 2.5 g (E)-3-(4-aminophenyl)-N-acetoxy-N-methyl-2-propenamide and 2.5 g acetonylacetone is heated at reflux in toluene using a Dean Stark water separator for 4 hours. The mixture is cooled, washed with water, brine and dried over magnesium sulphate. Concentration yields after purification (E)-3-[4-(2,5-dimethyl-1-H-pyrrol-1-yl)phenyl]-N-acetoxy-N-methyl-2-propenamide, the compound of Example 8.

The starting material is prepared as follows:

To a mixture of 34.4 g of p-bromoaniline in 400 ml of chloroform is added 200 ml of saturated sodium bicarbonate, followed by 51 g di-t-butyl dicarbonate in 50 ml of chloroform. The mixture is first stirred at room temperature for 4 hours and then heated under reflux overnight to yield 4-(t-butoxycarbonylamino)-bromobenzene, m.p. 101°-103°.

To a mixture of 27 g of 4-(t-butoxycarbonylamino)-bromobenzene, 0.18 g of palladium chloride, 1.25 g of tri-O-tolylphosphine and 50 ml of triethylamine is added 9.5 ml of acrylic acid followed by 25 ml of triethylamine. The reaction mixture is heated under reflux for 3 hours. Methylene chloride (250 ml) is added, the reaction mixture is filtered and evaporated to dryness. The residue is suspended in water, the suspension is washed with toluene, concentrated HCl is added while cooling to pH5. The resulting 4-(t-butoxycarbonylamino)-cinnamic acid is collected, washed with water and dried; m.p. 175°-177°.

Under conditions similar to those described in Example 1, 4-(t-butoxycarbonylamino)-cinnamic acid is converted to (E)-3-(4-t-butoxycarbonylaminophenyl)-N-hydroxy-N-methyl-2-propenamide, which is recrystallized from isopropanol-water; m.p. 220°-221° dec.

Acetyl chloride (0.7 ml) is added dropwise with stirring to an ice cold solution of 2 g (E)-3-(4-t-butoxy-carbonylamino-phenyl)-N-hydroxy-N-methyl-2-propenamide and triethylamine (1 ml) in dichloromethane. The mixture is stirred for 2 hours, then washed with ice cold 1N HCl, water, brine and dried over magnesium sulphate. Concentration to dryness yields (E)-3-(4-t-butoxycarbonyl-aminophenyl)-N-acetoxy-N-methyl-2-propenamide.

Dry hydrogen chloride gas is bubbled for 45 minutes through a stirred solution of 1.5 g (E)-3-(4-t-butoxycarbon-ylaminophenyl)-N-acetoxy-N-methyl-2-propenamide in anhydrous ethyl acetate which is cooled to −15°. Nitrogen gas is then bubbled through the solution to remove excess HCl and the solution is concentrated to yield the amine hydrochloride.

The salt is partitioned between ethyl acetate and saturated aqueous sodium bicarbonate solution. The organic phase is dried over magnesium sulphate and concentrated to yield the free base, (E)-3-(4-aminophenyl)-N-acetoxy-N-methyl-2-propenamide which is used immediately for the condensation with acetonylacetone.

EXAMPLE 10

To a solution of 3.12 g (E)-3-[4-(2,5-dimethyl-1-H-pyrrol-1-yl)phenyl]-N-acetoxy-N-methyl-2-propenamide in 2-propanol (50 ml) cooled to 0°, 1N aqueous lithium hydroxide (13 ml) is added with stirring. The mixture is stirred at room temperature for 30 minutes, then partitioned between ethyl acetate and 2N HCl. The organic phase is washed with brine, dried over magnesium sulphate and concentrated to dryness. Recrystallization from ethyl acetate yields (E)-3-[4-(2,5-dimethyl-1-H-pyrrol-1-yl)-phenyl]-N-hydroxy-N-methyl-2-propenamide of Example 1.

EXAMPLE 11 a) Preparation of 10,000 tablets each containing 20 mg of the active ingredient, having the formula as follows:

(E)-3-[4-(2,5-dimethyl-1H-pyrrol-1-yl)-phenyl]-N-hydroxy-N-methyl-2-propenamide:200.00 g
Lactose:2,535.00 g
Corn starch:125.00 g
Polyethylene glycol 6,000:150.00 g
Magnesium stearate:40.00 g
Purified water:q.s.

Procedure: All the powders are passed through a screen with openings of 0.6 mm. The drug substance, lactose, magnesium stearate and half of the starch are mixed in a suitable mixer. The other half of the starch is suspended in 65 ml of water and the suspension added to the boiling solution of the polyethylene glycol in 250 ml of water. The paste formed is added to the powders, which are granulated, if necessary, with an additional amount of water. The granulate is dried overnight at 35° C. broken on a screen with 1.2 mm openings and compressed into tablets, using concave punches uppers bisected.

Analogously tablets are prepared, containing about 1-100 mg of one of the other compounds disclosed and exemplified herein.

b) Preparation of 1,000 capsules each containing 10 mg of the active ingredient, having the formula as follows:

(E)-3-[4-(2,5-dimethyl-1H-pyrrol-1-yl)-phenyl]-N-hydroxy-N-methyl-2-propenamide:10.00 g
Lactose:207.00 g
Modified starch:80.00 g
Magnesium stearate:3.00 g Procedure: All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously capsules are prepared, containing about 1-100 mg of the other compounds disclosed and exemplified herein.

What is claimed is:

1. A compound of the formula

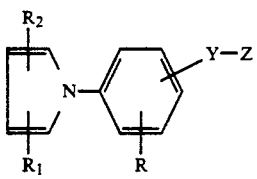

wherein R represents hydrogen, lower alkyl, halogen or lower alkoxy; $R_1$ and $R_2$ independently represent hydrogen, lower alkyl or aryl; Y represents a direct bond, lower alkylene, lower alkenylene, lower alkadienylene, (thio, sulfinyl or sulfonyl)-lower alkylene or oxy-lower alkylene; Z represents

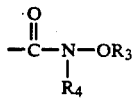

wherein $R_3$ represents hydrogen or acyl; $R_4$ represents lower alkyl, $C_3$-$C_7$-cycloalkyl, aryl or aryl-lower alkyl; or Z represents

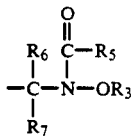

wherein $R_3$ represents hydrogen or acyl; $R_5$ represents lower alkyl, $C_3$-$C_7$-cycloalkyl, aryl, aryl-lower alkyl, amino or N-(mono- or di-lower alkyl)-amino; $R_6$ and $R_7$ represent hydrogen or lower alkyl; aryl in the above definitions represents phenyl of phenyl mono- or di-substituted by one or two radicals selected from lower alkyl, lower alkoxy, halogen, cyano and trifluoromethyl, or 1- 2-naphthyl; acyl represents lower alkanoyl or aroyl; and aroyl represents benzoyl or benzoyl mono- or di-substituted by one or two radicals selected from lower alkyl, lower alkoxy, halogen, cyano and trifluoromethyl, or 1- or 2-naphthoyl; or a pharmaceutically acceptable salt thereof provided that $R_3$ represents hydrogen.

2. A compound according to claim 1 of the formula

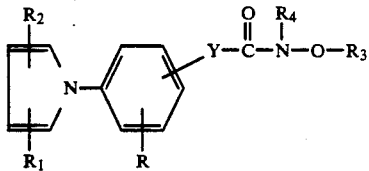

wherein R represents hydrogen, lower alkyl, halogen or lower alkoxy; $R_1$ and $R_2$ independently represent hydrogen, lower alkyl or aryl; $R_3$ represents hydrogen or acyl; $R_4$ represents lower alkyl, $C_3$-$C_7$-cycloalkyl, aryl or aryl-lower alkyl; Y represents a direct bond, lower alkylene, lower alkenylene, lower alkadienylene, (thio, sulfinyl or sulfonyl)-lower alkylene or oxy-lower alkylene; or a pharmaceutically acceptable salt of a said compound provided that wherein $R_3$ represents hydrogen.

3. A compound according to claim 1 of the formula

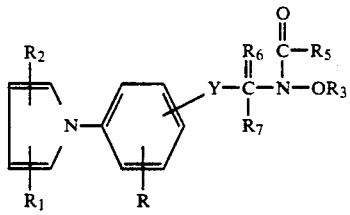

wherein R represents hydrogen, lower alkyl, halogen or lower alkoxy; $R_1$ and $R_2$ independently represent hydrogen, lower alkyl or aryl; Y represents a direct bond, lower alkylene, lower alkenylene, lower alkadienylene, (thio, sulfinyl or sulfonyl)-lower alkylene or oxy-lower alkylene; $R_3$ represents hydrogen or acyl; $R_5$ represents lower alkyl, $C_3$-$C_7$-cycloalkyl, aryl, aryl-lower alkyl, amino or N-(mono- or di-lower alkyl)-amino; $R_6$ and $R_7$ represent hydrogen or lower alkyl; or a pharmaceutically acceptable salt of a said compound provided that $R_3$ represents hydrogen.

4. A compound according to claim 2 wherein Y is located meta or para to the pyrrolyl ring.

5. A compound according to claim 3 wherein Y is located meta or para to the pyrrolyl ring.

6. A compound according to claim 4 of formula II wherein Y represents lower alkenylene, lower alkadienylene, lower alkylene, thio-lower alkylene or oxy-lower alkylene; R represents hydrogen or halogen; $R_1$ and $R_2$ independently represent hydrogen or lower alkyl; $R_3$ represents hydrogen or acyl; $R_4$ represents lower alkyl; or a pharmaceutically acceptable salt of a said compound provided that $R_3$ represents hydrogen.

7. A compound according to claim 4 of formula II wherein Y represents lower alkenylene, lower alkylene or oxy-lower alkylene; R represents hydrogen; $R_1$ and $R_2$ represent hydrogen or lower alkyl; $R_3$ represents hydrogen, lower alkanoyl or aroyl; $R_4$ represents lower alkyl; or a pharmaceutically acceptable salt thereof provided that $R_3$ represents hydrogen.

8. A compound according to claim 7 of formula II wherein Y represents lower alkenylene; or a pharmaceutically acceptable salt thereof provided that $R_3$ represents hydrogen.

9. A compound according to claim 8 of the formula

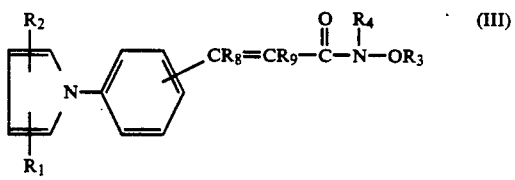

wherein $R_1$, $R_2$ and $R_8$ and $R_9$ independently represent hydrogen, methyl or ethyl; $R_4$ represents $C_1$-$C_3$-alkyl; $R_3$ represents hydrogen; or a pharmaceutically acceptable salt thereof.

10. A compound according to claim 9 of the formula

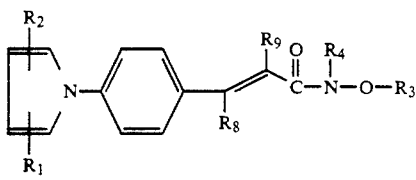

(IV)

wherein $R_1$, $R_2$ and $R_8$ and $R_9$ independently represent hydrogen, methyl or ethyl; $R_4$ represents $C_1$–$C_3$-alkyl; $R_3$ represents hydrogen; or a pharmaceutically acceptable salt thereof.

11. A compound according to claim 10 of formula IV wherein $R_1$, $R_2$ and $R_4$ represent methyl or ethyl; $R_3$, $R_8$ and $R_9$ represent hydrogen; or a pharmaceutically acceptable salt thereof.

12. A compound according to claim 10 being (E)-3-[4-(2,5-dimethyl-1H-pyrrol-1-yl)-phenyl]-N-hydroxy-N-methyl-2-propenamide or a pharmaceutically acceptable salt thereof.

13. A compound according to claim 5 of formula V wherein Y represents a direct bond, thio-lower alkylene, oxy-lower alkylene, lower alkenylene or lower alkylene; R represents hydrogen; $R_1$ and $R_2$ independently represent hydrogen or lower alkyl; $R_3$ represents hydrogen, lower alkanoyl or aroyl; $R_5$ represents lower alkyl, aryl-lower alkyl, N-(mono- or di-lower alkyl)-amino or amino; $R_6$ represents hydrogen; $R_7$ represents hydrogen or lower alkyl; or a pharmaceutically acceptable salt thereof provided that $R_3$ represents hydrogen.

14. A compound according to claim 13 wherein Y represents a direct bond, lower alkylene or lower alkenylene.

15. A compound according to claim 13 of the formula

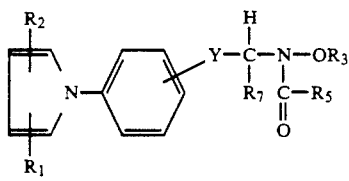

(VI)

wherein $R_1$ and $R_2$ represents hydrogen or lower alkyl; Y represents a direct bond, methylene or ethylene; $R_3$ represents hydrogen; $R_5$ represents $C_1$–$C_3$-alkyl, N-(mono- or di-lower alkyl)-amino or amino; $R_7$ represents hydrogen or $C_1$–$C_3$-alkyl; or a pharmaceutically acceptable salt thereof.

16. A compound according to claim 13 of formula VII

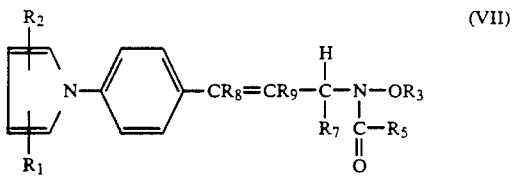

(VII)

wherein $R_1$, $R_2$, $R_7$, $R_8$ and $R_9$ represent hydrogen, methyl or ethyl; $R_3$ represents hydrogen; $R_5$ represents $C_1$–$C_3$-alkyl, N-(mono- or di-lower alkyl)-amino or amino; or a pharmaceutically acceptable salt thereof.

17. A compound according to claim 15 being N-acetyl-N-hydroxy-1-[4-(2,5-dimethyl-1H-pyrrol-1-yl)-phenyl]-ethyl-amine or a pharmaceutically acceptable salt thereof.

18. A compound according to claim 13 being N-carbamoyl-N-hydroxy-4-(2,5-dimethyl-1H-pyrrol-1-yl)-cinnamyl-amine or a pharmaceutically acceptable salt thereof.

19. A compound according to claim 8 being (E)-3-[4-(2,5-dimethyl-1H-pyrrol-1-yl)-phenyl]-N-acetoxy-N-methyl-2-propenamide.

20. A pharmaceutical composition suitable for inhibiting 5-lipoxygenase activity in mammals comprising an effective 5-lipoxygenase inhibiting amount of a compound of claim 1 in combination with one or more pharmaceutically acceptable carriers.

21. A method of inhibiting lipoxygenase activity and of treating disorders in mammals which are responsive to such inhibition which comprises administering to a mammal in need thereof an effective lipoxygenase inhibiting amount of a compound of claim 1 or of a said compound in combination with one or more pharmaceutically acceptable carriers.

22. A method of inhibiting lipoxygenase activity and of treating disorders in mammals which are responsive to such inhibition which comprises administering to a mammal in need thereof an effective lipoxygenase inhibiting amount of a compound of claim 12 or of a said compound in combination with one or more pharmaceutically acceptable carriers.

* * * * *